United States Patent [19]

Hamprecht

[11] Patent Number: 4,888,432
[45] Date of Patent: Dec. 19, 1989

[54] PROCESS FOR PREPARING 2-AMINO-THIOPHENES AND AZO DYESTUFFS PREPARED THEREFROM

[75] Inventor: Rainer Hamprecht, Odenthal, Fed. Rep. of Germany

[73] Assignee: Bayer Aktiengesellschaft, Leverkusen, Fed. Rep. of Germany

[21] Appl. No.: 109,022

[22] Filed: Oct. 15, 1987

[30] Foreign Application Priority Data

Nov. 3, 1986 [DE] Fed. Rep. of Germany ....... 3637223

[51] Int. Cl.$^4$ ............... C07C 153/00; C07C 153/063; C07D 333/00; C07D 333/68
[52] U.S. Cl. ...................................... 549/57; 534/573; 534/768; 534/787; 549/55; 558/388; 558/408
[58] Field of Search ................ 534/768, 787; 549/57, 549/55

[56] References Cited

U.S. PATENT DOCUMENTS

| | | | |
|---|---|---|---|
| 3,491,083 | 1/1970 | Mangini et al. ................ | 549/57 X |
| 3,776,924 | 12/1973 | Lundberg et al. ............... | 549/57 X |
| 4,013,681 | 3/1977 | Karabinos et al. .............. | 549/57 |
| 4,055,556 | 10/1977 | Aeberli ........................... | 534/787 X |
| 4,092,329 | 5/1978 | Jotterand ........................ | 534/787 X |
| 4,507,407 | 3/1985 | Kluger et al. .................... | 534/768 X |
| 4,668,775 | 5/1987 | Bergmann et al. .............. | 534/768 X |

FOREIGN PATENT DOCUMENTS

| | | | |
|---|---|---|---|
| 0166566 | 1/1986 | European Pat. Off. ............ | 534/753 |
| 2333447 | 1/1974 | Fed. Rep. of Germany ...... | 534/753 |
| 2757422 | 6/1978 | Fed. Rep. of Germany ...... | 549/57 |

OTHER PUBLICATIONS

Beck et al., J. Org. Chem., vol. 39, pp. 3440–3441, (1974).
Gewald et al., Ber. Deut. Chem. Gesell., vol. 101, pp. 1933–1939, (1968).
Pallos et al., Chemical Abstracts, vol. 78, #29282q, (1973).
Chemische Berichte, Band 101, No. 6, 1968, Seiten 1933–1939, Verlag Chemie GmbH, Wwinheim, DE; K. Gewald et al.: "2-Amino-thionaphthene".

*Primary Examiner*—Floyd D. Higel
*Attorney, Agent, or Firm*—Sprung Horn Kramer & Woods

[57] ABSTRACT

2-Aminothiophenes of the formula

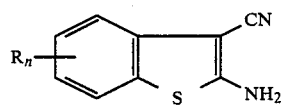

wherein R=substituent and n=0–4, are prepared by dehydrogenating ring closure of thioamides of the formula

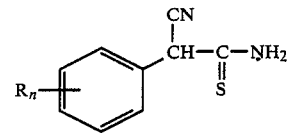

The 2-aminothiophenes are useful for preparing useful azo dyestuffs.

A process for preparing a compound of the formula

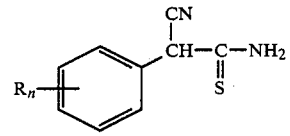

comprising reacting a compound of the formula

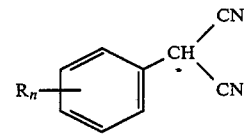

in which R and n have the abovementioned meanings with a compound of the formula

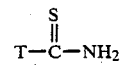

in which T denotes NH$_2$, aryl or alkyl, in the presence of an acid.

An azo dyestuff of the formula

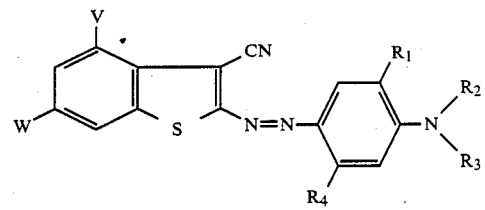

in which
V denotes Cl, Br or CF$_3$,
W denotes Cl, Br or NO$_2$,
R$_1$ denotes hydrogen, halogen, alkyl, alkoxy, alkoxyalkyl or aryloxy,
R$_2$ denotes alkenyl or OH-, halogen-, CN-, CO$_2$-alkyl-, aryl-, cycloalkyl-, alkoxy-, aryloxy-, OCO-alkyl-, OCO-aryl-, OCONH-alkyl- or OCO$_2$-alkyl-substituted alkyl,
R$_3$ denotes hydrogen or identical or different R$_2$ and
R$_2$ denotes hydrogen, alkyl, alkenyl, cycloalkyl, aralkyl, alkoxy, halogen, CF$_3$ NHCO-alkyl, NHCO-aryl, NHCO$_2$-alkyl, NHCHO, NHSO$_2$-alkyl, NHCONH$_2$, NHSO$_2$-aryl, NHSO$_2$-alkenyl, NHCONH-alkyl or NHCON-(alkyl)$_2$.

8 Claims, No Drawings

PROCESS FOR PREPARING 2-AMINO-THIOPHENES AND AZO DYESTUFFS PREPARED THEREFROM

The invention relates to a process for preparing 2-aminothiophenes of the formula

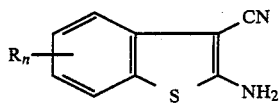

in which
R denotes a substituent and
n denotes a number from 0 to 4.

It is already known to prepare compounds of this type by the so-called "Gewald reaction" and subsequent aromatization (cf. Chem. Ber. 98, 3571 (1965) and 101, 1933 (1968)).

The principle of this synthesis may be illustrated by way of example by reference to the following reaction scheme:

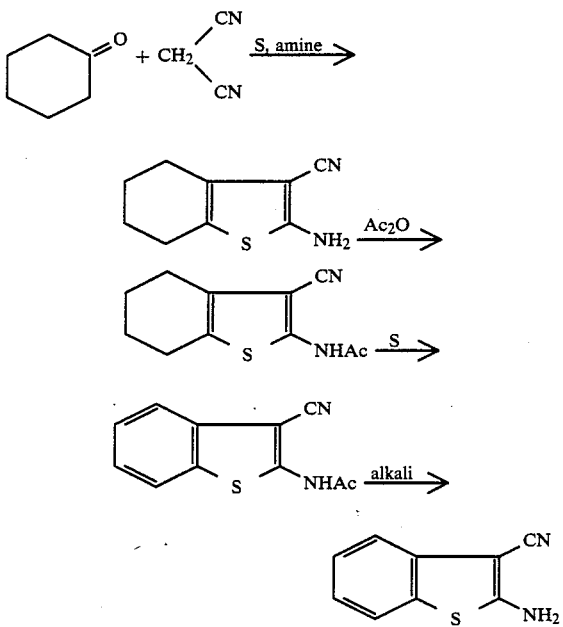

However, this original method has the disadvantage that it involves many stages, of which in particular the first and penultimate stages only produce comparatively low yields. The overall yield (based on cyclohexanone) is therefore only scarcely 10%.

It has now been found that 2-aminothiophenes of formula (I) are obtained significantly more advantageously when thioamides of the formula

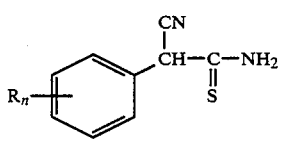

(II)

are reacted with dehydrogenating agents to give ring closure.

Suitable substituents R in the formulae (I) and (II) are in particular nonionic types as customary in particular in dyestuff chemistry.

Specific examples are: F, Cl, Br, I, $C_1$-$C_4$-alkyl, $NO_2$, CN, $SO_2$-$C_1$-$C_4$-alkyl and $CF_3$.

In addition, two adjacent radicals R can together form a fused-on carbocyclic or heterocyclic ring.

Preferred process products conform to the formula

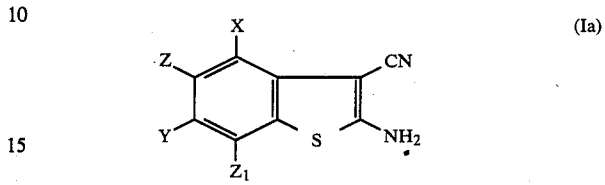

in which
X denotes H, Cl, Br, $CF_3$ or $SO_2$-$C_1$-$C_2$-alkyl,
Y denotes H, Cl, Br or $NO_2$ and
$Z/Z_1$ denotes Cl, Br and in particular H.

Suitable dehydrogenating agents for carrying out the cyclization according to the invention are in particular free halogen ($I_2$, $Br_2$ or $Cl_2$) and halogen-eliminating compounds (for example N-bromosuccinimide).

Preference is given to iodine and in particular bromine.

In general, it may be used in equimolar amounts.

The reaction can be carried out within a wide temperature range (about $-20°$ to $100°$ C.). Preference is given to working at room temperature, i.e. at about $10°$ to $30°$ C.

Expediently, the reaction is carried out in a suitable solvent which is inert under reaction conditions. Preference is given to organic solvents, such as, for example, methanol, ethanol, isopropanol, $CH_2Cl_2$, $C_2H_2Cl_2$, $CHCl_3$, $CCl_4$, toluene or chlorobenzene.

Particular preference is given to apolar types.

As for the rest, it is advisable to carry out the ring closure reaction in the presence of an acid acceptor, such as, for example, organic and inorganic bases.

Suitable bases are: trialkylamine, pyridine and alkali metal and alkaline earth metal oxides, hydroxides, carbonates and preferably hydrogencarbonates, such as, for example, $NaHCO_3$.

In practice the process is carried out for example by adding a solution of bromine in methylene chloride dropwise at room temperature to a solution or dispersion of the thioamide and of the sodium hydrogencarbonate in methylene chloride and subsequently stirring until the reaction has ended.

It has to be considered a complete surprise that this ring closure proceeds so smoothly since, on the basis of similar known reactions (cf. J. Org. Chem. 31, 2654 (1966)), it was possible to expect that at least some of the starting material would undergo dimerization to form compounds of the following formula:

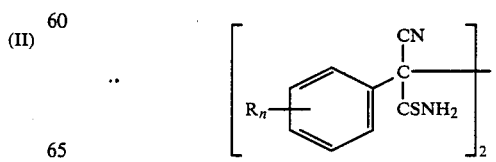

The thioamides of the formula (II) have hitherto not been described in the literature. It has now been found in the context of a further subject-matter of this invention that the novel compounds are easily obtained when compounds of the formula

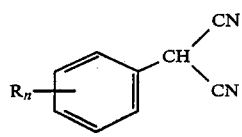

are reacted with compounds of the formula

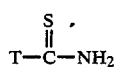

in which

T denotes NH$_2$, aryl or alkyl, preferably methyl, in the presence of an acid.

This reaction too is advantageously carried out in a solvent. In this case, however, in particular dipolar aprotic solvents, such as, for example, DMF, are suitable.

Suitable acids are in particular halohydric acids, such as, for example, hydrogen chloride.

The compounds of the formula (IV), preferably thioacetamide, are used in equimolar amounts and up to an excess of 100%.

It is surprising that the reaction of (III) with (IV)—contrary to other findings on similar systems (cf. J.A.C.S 82, 2656 (1960))—only produces the monothiamide even if an excess of (IV) is present.

This unforeseeably problem-free reaction produces, depending on the nature of the starting material used, total yields of the process product of the formula (I) over all stages (i.e. 1st preparation of (III), 2nd reaction of (III) with (IV), 3rd cyclization of (II)) of 40 to 60%.

This is a significant yield improvement compared with the known "Gewald process", which—as shown above— only gives yields of less than 10%, and even that only in the case of the unsubstituted type where R$_n$=H.

The preparation of the compounds of the formula (III) required as starting material is effected by methods known per se (cf. German Pat. No. 2,854,197=GB No. 2,037,286; J.A.C.S. 72, 1853 (1950), and 74, 3443 (1952), and also H. Hindermayr, Doctoral Thesis, Ludwig Maximilian University, Munich 1967) and is illustrated in detail in the examples below.

The process products of the formula (I) are diazo components which can be converted by conventional methods into partly known azo dyestuffs (cf. German Pat. No. 2,333,447=GB No. 1,434,654).

The present invention further relates to novel azo dyestuffs of the formula

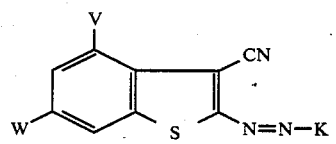

in which

K denotes a radical of the formulae

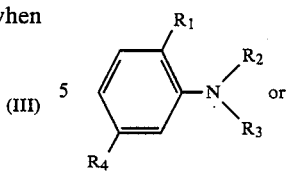

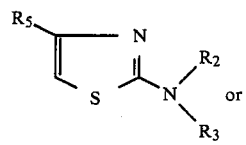

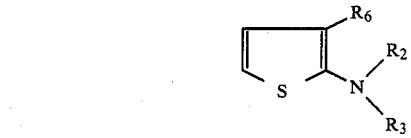

V denotes Cl, Br or CF$_3$,

W denotes Cl, Br or NO$_2$,

R$_1$ denotes hydrogen, halogen, alkyl, alkoxy, alkoxyalkyl or aryloxy,

R$_2$ denotes alkenyl or optionally OH-, halogen-, CN-, CO$_2$-alkyl-, aryl-, cycloalkyl-, alkoxy-, aryloxy-, OCO-alkyl-, OCO-aryl-, OCONH-alkyl- or OCO$_2$-alkyl-substituted alkyl, R$_3$ denotes hydrogen or identical or different R$_2$ and R$_4$ denotes hydrogen, alkyl, alkenyl, cycloalkyl, aralkyl, alkoxy, halogen, CF$_3$, NHCO-alkyl, NHCO-aryl, NHCO$_2$-alkyl, NHCHO, NHSO$_2$-alkyl, NHCONH$_2$, NHSO$_2$-aryl, NHSO$_2$-alkenyl, NHCONH-alkyl or NHCON(alkyl)$_2$ R$_5$ denotes hydrogen, alkyl, aralkyl, cycloalkyl, hetaryl or in particular aryl and R$_6$ denotes CN or CO$_2$-alkyl, it being possible for the hydrocarbon radicals mentioned to be substituted by further customary substituents known in the chemistry of azo dyestuffs.

The alkyl radicals mentioned above in no particular context are preferably to be understood as being those having 1 to 8, in particular 1 to 4, C atoms. Particular preference is given to methyl, ethyl and methoxy.

Suitable aryl and aryloxy radicals are in particular phenyl and phenoxy radicals which can be substituted by C$_1$-C$_4$-alkyl, halogen, CO$_2$-C$_1$-C$_4$-alkyl, NO$_2$, COCH$_3$, C$_1$-C$_4$-alkoxy or CN.

Suitable aralkyl radicals are phenyl-C$_1$-C$_3$-alkyl radicals which, like the aryl radicals, can contain a sulphur group.

Suitable cycloalkyl radicals are cyclohexyl radicals.

The alkenyl radicals mentioned preferably have 3 to 6 C atoms.

"Halogen" refers in particular to Br and Cl.

Preferred dyestuffs are those of the formula (V) wherein

R$_1$ denotes hydrogen, alkyl, alkoxy or Cl,

R$_2$ denotes alkenyl or Cl-, CN-, CO$_2$-alkyl-, aryl-, alkoxy-, OCO-alkyl-, OCO$_2$-alkyl- or OCO-aryl-substituted alkyl, R$_3$ denotes hydrogen or identical or different preferred R$_2$, R$_4$ denotes hydrogen, alkyl, alkoxy, Cl or—in particular —NHCO-alkyl, NHCO-phenyl, NHCO$_2$-alkyl, NHSO$_2$-alkyl or NHSO$_2$-aryl and where the alkyl, alkoxy, alkenyl and aryl radicals mentioned have for example the abovementioned numbers of C and substitution patterns.

Particularly preferred dyestuffs conform to the formula (V) wherein $R_1$ denotes H, $C_1$–$C_2$-alkoxy, $CH_3$ or Cl, $R_2$ denotes $C_3$–$C_6$-alkenyl or optionally OH-, Cl-, CN-, $CO_2$-$C_1$–$C_2$-alkyl-, phenyl-, tolyl-, chlorophenyl-, $C_1$–$C_4$-alkoxy-, OCO-$C_1$–$C_4$-alkyl-, OCO-phenyl-, OCO-tolyl- or OCO-chlorophenyl-substituted $C_1$–$C_6$-alkyl, $R_3$ denotes H or $C_1$–$C_6$-alkyl which is optionally substituted by CN, $CO_2$-$C_1$–$C_2$-alkyl, phenyl, tolyl, chlorophenyl, $C_1$–$C_4$-alkoxy, OCO-$C_1$–$C_4$-alkyl, OCO-phenyl, OCO-tolyl or OCO-chlorophenyl, and $R_4$ denotes H, $CH_3$ or—in particular —NHCO-$C_1$–$C_4$-alkyl, NHCO-phenyl, NHCO-tolyl, NHCO-chlorophenyl, $NHSO_2$-$C_1$–$C_4$-alkyl, $NHSO_2$-$CH_2$Cl, $NHCO_2$-$C_1$–$C_4$-alkyl, $NHSO_2$-phenyl, $NHSO_2$-tolyl or $NHSO_2$-chlorophenyl.

Further novel dyestuffs obtainable by the process according to the invention for preparing benzothiophenes are the following:

(a) dyestuffs of the formula

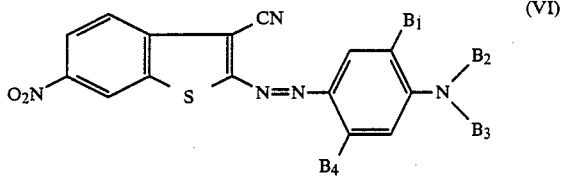

in which $B_1$ denotes H, Cl or $OCH_3$, $B_2$ denotes $C_2$–$C_4$-alkyl, $C_2H_4OCH_3$, $C_2H_4OC_2H_5$, $C_2H_4OCOCH_3$ or $C_2H_4OCOC_2H_5$, $B_3$ denotes identical or different $B_2$, $B_4$ denotes $NHCOB_5$ and $B_5$ denotes H or $C_1$–$C_4$-alkyl.

(b) Dyestuffs of the formula (VI) in which $B_1$ denotes H or $OCH_3$, $B_2$ denotes $C_2$–$C_4$-alkyl, $B_3$ denotes $B_2$ or $C_2H_4CN$, $B_4$ denotes $NHCOB_5$ and $B_5$ denotes $C_1$–$C_4$-alkyl.

Preferably, $B_1$ stands for H and $B_5$ for $C_2$–$C_4$-alkyl. The novel dyestuffs are obtained by diazotization and coupling in a conventional manner.

The novel dyestuffs are highly suitable for dyeing and printing textile fibre materials, the water-insoluble types naturally being used for dyeing hydrophobic fibres, such as cellulose esters, polyesters or mixtures of these materials with natural fibre materials but also for colouring organic solvents, mineral oil products, waxes, plastics and surface coatings.

On the preferred polyester fibres the novel dyestuffs produce deep brilliant dyeings and prints having good fastness properties, in particular good light and sublimation fastness properties.

EXAMPLE 1

(a) Preparation of 2-amino-3-cyano-6-nitrobenzo-[b]-thiophene of the formula

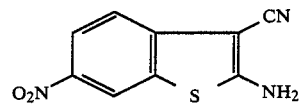

A solution of 1.3 ml (25 mmol) of bromine in 10 ml of dichloroethane is added dropwise to a suspension of 5.53 g (25 mmol) of p-nitrophenylcyanothioacetamide and 4.2 g (50 mmol) of sodium hydrogencarbonate in 40 ml of 1,2-dichloroethane. The temperature is maintained at 20° C. by cooling with ice-water. This is followed by 30 minutes of stirring, filtering off with suction and washing with water. Drying in vacuo at 50° C. leaves 4.9 g of a brown powder=89% of theory.

$M_e+$: 219; melting point: 266° C.

IR: 3390 cm$^{-1}$ ($NH_2$); 2217 cm$^{-1}$ (C≡N) 1328 cm$^{-1}$ ($NO_2$).

$^1$H-NMR (DMSO): δ=7.35 ppm (d, J=7.5 Hz, 1H), 8.06 ppm (dd, J=7.5 Hz, J=2.5 Hz, 1H), 8.46 ppm (s, 2H, replaceable with $D_2O$), 8.65 ppm (d, J=2.5 Hz, 1H).

(b) Preparation of p-nitrophenylcyanothioacetamide

A solution of 187 g of p-nitrophenylmalodinitrile and 75 g of thioacetamide in 1 l of dimethylformamide is saturated at room temperature with hydrogen chloride and heated to 100° C. while further hydrogen chloride is passed in slowly. This is followed by stirring at 100° C. for 90 minutes. After cooling down, the solution is discharged onto 4 l of ice-water, while the pH value is maintained at 10 to 11 by adding concentrated sodium hydroxide solution. A small residue is filtered off, and the filtrate is acidified by adding concentrated hydrochloric acid to pH 2 while cooling. To obtain better crystallization, this is followed by stirring overnight at room temperature, filtering off with suction and drying.

Yield: 143 g (65% of theory);

$M_e+$: 221 (11%) $C_9H_7N_3O_2S$.

Melting point: 75° C.

(c) Preparation of p-nitrophenylmalodinitrile 198 g of malodinitrile are added to a solution of 120 g of pulverulent NaOH in 1.5 of dimethylformamide, followed at room temperature by dropwise addition of a solution of 236 g of 4-nitrochlorobenzene in 150 ml of DMF. After two days of stirring at room temperature, the solvent is substantially removed in vacuo, and the residue is dissolved in 5 l of ice-water. While cooling, pH 2 is set with hydrochloric acid, and the resulting precipitate is filtered off with suction and dried in vacuo at 50° C.

Yield: 240 g of orange powder (crude yield: 85% of theory).

EXAMPLE 2

(a) Preparation of 2-amino-3-cyano-4-chloro-6-nitrobenzo-[b]-thiophene of formula

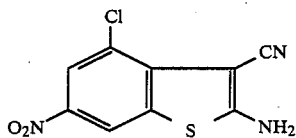

A solution of 9.2 ml (0.18 mol) of bromine in 72 ml of methylene chloride is added dropwise at room temperature to a suspension of 46 g of 2-chloro-4-nitrophenylcyanothioacetamide (0.18 mol) and 30 g of sodium hydrogencarbonate (0.36 mol) in 650 ml of methylene chloride. This was followed by 2 hours of stirring at room temperature, filtering off with suction and repeated washing of the yellow residue with water.

Yield: 43 g = 94% of theory;
$M_e+253$ (100%); 255 (33.8%) ($C_9H_4ClN_3O_2S$),
Melting point: 279° C., (b) Preparation of 2-chloro-4-nitrophenylcyanothioacetamide A solution of 66.5 g (0.3 mol) of 2-chloro-4-nitrophenylmalodinitrile and 22.5 g (0.3 mol) of cyanothioacetamide in 300 ml of dimethylformamide is saturated at room temperature with hydrogen chloride and heated to 100° C. while further hydrogen chloride is passed in. Two hours at 100° C. is followed by cooling down and discharging onto 1.5 l of ice-water, a pH of 10.5 being maintained by adding concentrated sodium hydroxide solution. An insoluble residue is filtered off, and the ice-cooled filtrate is slowly acidified with concentrated hydrochloric acid to pH 2. The initially oily precipitate becomes crystalline overnight.

Yield: 55 g = 72% of theory;
$M_e+$: 255 ($C_9H_6ClN_3O_2S$),
Melting point: 148° C.,
$^1$H-NMR (DMSO)δ = 5.9 ppm (s, 1H exchangeable with D$_2$O), 7.85 ppm (d, 1H), 8.28 ppm (m, 2H), 9.75 ppm (s, 1H, exchangeable with D$_2$O), 10.23 ppm (s, 1H, exchangeable with D$_2$O):

(c) Preparation of 2-chloro-4-nitrophenylmalodinitrile

A solution of 96 g (0.5 mol) of 1,2-dichloro-4-nitrobenzene in 100 ml of dimethylformamide was added dropwise at 0° C. to a solution of 40 g of pulverulent sodium hydroxide and 66 g (1 mol) of malodinitrile in 1 l of dimethylformamide in the course of one hour. This was followed by two days of stirring at room temperature, removal of the solvent in vacuo and discharge of the residue onto 4 l of ice-water. While cooling, the solution was gradually brought to pH 1.5 by the dropwise addition of concentrated hydrochloric acid. This was followed by filtering off with suction and washing with 1N hydrochloric acid. Drying was carried out in vacuo at 50° C.

Yield: 105 g (95% of theory);
$M_e+$: 221 (54%), 223 (18%).
$^1$H-NMR (DMSO): δ = 6.95 ppm (d, J = 9 Hz, 1H), 7.83 ppm (m, 2H), 12.5 ppm (s broad, 1H).
Melting point: 105° C.

EXAMPLE 3

(a) Preparation of 2-amino-3-cyano-4-trifluoromethyl-6-nitrobenzo-[b]-thiophene

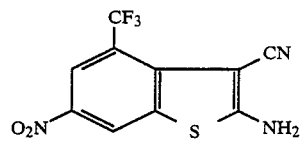

The procedure is analogous to that of Example 2a.
Yield: 60% of theory;
$M_e+$: 287 (199%) $C_{10}H_4F_3N_3O_2S$.
Melting point: 257° C.

(b) Preparation of 2-trifluoromethyl-4-nitrophenylcyanothioacetamide as a starting material for Example 3a.

A solution of 230 g of 2-trifluoromethyl-4-nitrophenylmalodinitrile in 900 ml of dimethylformamide is saturated at room temperature with hydrogen chloride. Addition of 74.4 g of thioacetamide is followed by heating at 100° C. for 2 hours. This is followed by cooling at room temperature and pouring onto 6 l of ice-water, pH 10 to 11 being maintained by adding sodium hydroxide solution. After a clarifying filtration, the filtrate is gradually brought to pH 2 with concentrated hydrochloric acid while cooling. The semicrystalline precipitate is separated off and stirred overnight with 2 l of water and 1 l of methanol. This is followed by filtering off with suction and washing with 1N hydrochloric acid.

Yield: 191 g (65% of theory).
Melting point: 73° C.

(c) Preparation of 2-trifluoromethyl-4-nitrophenylmalodinitrile

The procedure is analogous to Example 1c, affording a yield of 93% of theory; melting point: 103° C.

EXAMPLE 4

Preparation of 2-amino-3-cyano-4-methylsulphonyl-6-nitrobenzo-[b]-thiophene of the formula

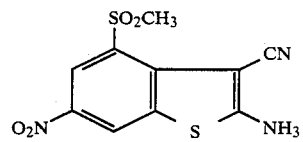

The synthesis is effected analogously to Example 1 from 2-methylsulphonyl-4-nitrophenylcyanothioacetamide. The crude product is recrystallized from dimethylformamide.

$M_e+$: 297 (100%) $C_{10}H_7N_3O_4S_2$.
IR: 2200 cm$^{-1}$ (C≡N).
$^1$H-NMR (DMSO) δ = 3.30 ppm (s, 4H, —NH$_2$, H$_2$O), 3.45 ppm (s, 3H), 8.60 ppm (d, J = 2 Hz, 1H), 8.85 ppm (s, broad, 1H), 9.05 ppm (d, J = 2 Hz, 1H).

EXAMPLE 5

Preparation of 2-amino-3-cyano-6,7-dichlorobenzo-[b]-thiophene of the formula

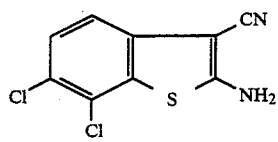

By reacting 3,4-dichlorophenylmalodinitrile with thioacetamide analogously to Example 1, 3,4-dichlorophenylcyanothioacetamide is obtained in a 63% yield. Melting point: 143° C. (3,4-dichlorophenylmalonitrile is obtainable by reaction of 3,4-dichlorobenzyl cyanide with dimethyl carbonate/sodium methylate, further reaction with chlorine cyanide, hydrolysis and decarboxylation).

The ring closure of 3,4-dichlorophenylcyanothioacetamide to give 2-amino-3-cyano-6,7-dichlorobenzo-[b]-thiophene is effected analogously to Example 6 in a 69% yield. The product is recrystallizable from dimethylformamide.

$M_e+$: 242 (100%), 243 (12%), 244 (76%), 245 (7%), 246 (7%), 246 (14%) ($C_9H_4Cl_2N_2S$).

Melting point: 262° C.

$^1$H-NMR (DMSO) $\delta$=7.2 ppm (d, J=7.5 Hz, 1H), 7.48 ppm (d, J=7.5 Hz, 1H), 8.18 ppm (s, 2H, exchangeable with $D_2O$).

EXAMPLE 6

Preparation of a dyestuff of the formula

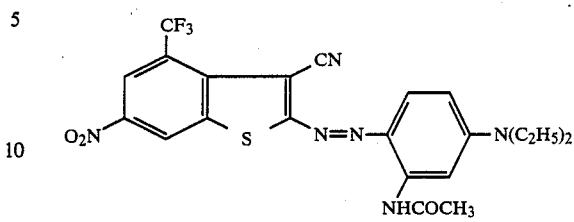

5 ml of 42% strength nitrosylsulphuric acid is added dropwise at 0° C. to a solution of 8.3 g of 2-amino-3-cyano-4-trifluoromethyl-6-nitrobenzo-[b]-thiophene in 20 ml of propionic acid and 40 ml of glacial acetic acid in the course of 15 minutes. After 30 minutes of stirring, the diazotization solution is then added to an ice-cold (0° C.) solution of 3-diethylaminoacetanilide in 20 ml of 10% strength aqueous sulphamic solution in 100 ml of glacial acetic acid in the course of 5 minutes. Dilution with ice-water to a volume of 900 ml is followed by 2 hours of stirring at 0° C., filtering off with suction, washing with water until acid-free and drying. Yield: 10.6 g (72% of theory). After redissolving in dimethylformamide and reprecipitation the dyestuff has a melting point of 261° C. $\lambda_{max}$=611 nm (DMF). The dyestuff dyes polyester by the HT method in a bright blue having very good fastness properties.

Analogous or similar processes can be used to obtain the following dyestuffs:

| Example No. | | $\lambda_{max}$ (DMF) | Hue on polyester |
|---|---|---|---|
| 7 | | 610 | blue |
| 8 | | 624 | blue |
| 9 | | | greenish blue |

| Example No. | | $\lambda_{max}$ (DMF) | Hue on polyester |
|---|---|---|---|
| 10 | 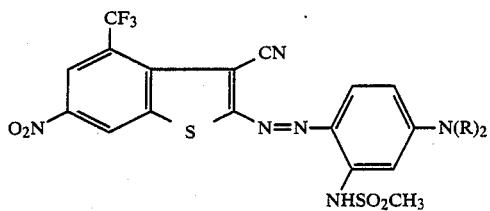<br>50% R = C₂H₅<br>50% R = n-C₃H₇ | | blue |
| 11 | 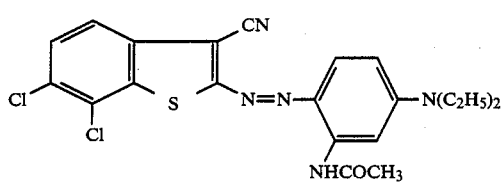 | | violet |
| 12 | 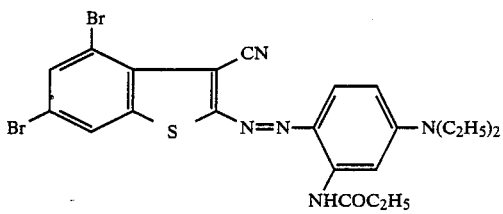 | | violet |
| 13 | 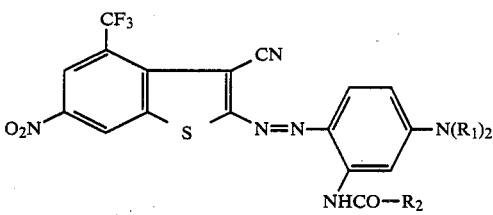 | | blue |
|  | R₁ | R₂ |
|---|---|---|
| 25% | C₂H₅ | CH₃ |
| 25% | C₃H₇ | CH₃ |
| 25% | C₂H₅ | C₂H₅ |
| 25% | C₂H₅ | n-C₃H₇ |
| Example No. | | $\lambda_{max}$ (DMF) | Hue on polyester |
|---|---|---|---|
| 14 | 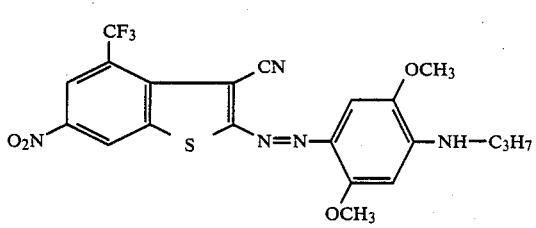 | | greenish blue |
| 15 | 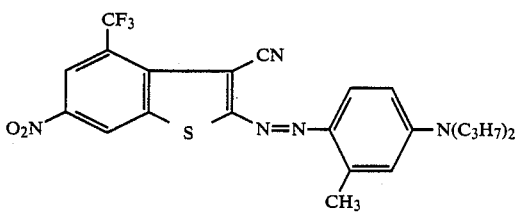 | | blue |

-continued

| Example No. | Structure | λmax (DMF) | Hue on polyester |
|---|---|---|---|
| 16 | 4-CF₃, 6-O₂N-benzothiophene-3-CN, 2-N=N-[4-N(C₂H₅)₂, 2-NHCOCH₂OCOCH₃]phenyl | | greenish blue |
| 17 | 4-CF₃, 6-O₂N-benzothiophene-3-CN, 2-N=N-[4-N(C₂H₄OCOCH₃)₂, 2-NHCOC₂H₅]phenyl | | reddish blue |
| 18 | 4-CF₃, 6-O₂N-benzothiophene-3-CN, 2-N=N-[4-N(C₂H₄OC₂H₅)₂, 2-NHCOCH₃]phenyl | | blue |
| 19 | 4-Cl, 6-O₂N-benzothiophene-3-CN, 2-N=N-[4-N(C₂H₄OCH₃)₂, 2-NHCOC₂H₅]phenyl | | blue |
| 20 | 4-Cl, 6-O₂N-benzothiophene-3-CN, 2-N=N-[4-N(C₂H₄OCOC₂H₅)₂, 2-NHCOC₂H₅]phenyl | | reddish blue |
| 21 | 4-Cl, 6-O₂N-benzothiophene-3-CN, 2-N=N-[4-N(C₃H₇)₂, 2-NHCOCH₂OC₂H₅]phenyl | | greenish blue |
| 22 | 4-Cl, 6-O₂N-benzothiophene-3-CN, 2-N=N-[4-N(C₂H₄OCOCH₃)₂, 5-OCH₃, 2-NHCOCH₃]phenyl | | strongly greenish blue |

| Example No. | Structure | λ_max (DMF) | Hue on polyester |
|---|---|---|---|
| 23 | 3-Cl, 6-NO₂-benzothiophene-2-yl, with CN at 3-position, azo-linked to 2-(NHSO₂CH₃)-4-N(C₂H₅)₂-phenyl | | blue |
| 24 | 3-Cl, 6-NO₂-benzothiophene-2-yl, with CN at 3-position, azo-linked to 4-N[(CH₂)₃CH₃]₂-phenyl | | blue |
| 25 | 4-CF₃, 6-NO₂-benzothiophene-2-yl, with CN at 3-position, azo-linked to 2-(NHCO—R)-4-N(C₂H₅)₂-phenyl; R = CH₃, C₂H₅, C₃H₇ | | blue |
| 26 | 4-Cl, 6-NO₂-benzothiophene-2-yl, with CN at 3-position, azo-linked to 4-N[(CH₂)₃CH₃]₂-phenyl | | reddish blue |
| 27 | 4-Cl, 6-NO₂-benzothiophene-2-yl, with CN at 3-position, azo-linked to 3-CH₃-4-N(C₂H₅)(C₂H₄CN)-phenyl | | reddish blue |
| 28 | 3-Cl, 6-NO₂-benzothiophene-2-yl, with CN at 3-position, azo-linked to 2-(NHCOC₂H₅)-4-N(C₂H₅)₂-phenyl | | blue |
| 29 | 3-Cl, 6-NO₂-benzothiophene-2-yl, with CN at 3-position, azo-linked to 2-[NHCO(CH₂)₂CH₃]-4-N(C₂H₅)₂-phenyl | | blue |

-continued

| Example No. | Structure | λ_max (DMF) | Hue on polyester |
|---|---|---|---|
| 30 | 4-Cl, 6-O₂N-benzo[b]thiophene-3-CN, 2-position N=N-C₆H₃(NHCO(CH₂)₃CH₃)-N(C₂H₅)₂ | | blue |
| 31 | 4-Cl, 6-O₂N-benzo[b]thiophene-3-CN, 2-position N=N-C₆H₃(NHCOCH₃)-N(C₃H₇)₂ | | blue |

EXAMPLES 32–39

Example 6 is repeated, except that the diazo component used is 2-amino-3-cyano-6-nitrobenzo-[b]-thiophene which, after diazotization, is combined with appropriate coupling components, affording the dyestuffs listed in the table below:

| Example No. | Structure | λ_max (DMF) | Hue on polyester |
|---|---|---|---|
| 32 | 6-O₂N-benzo[b]thiophene-3-CN, 2-N=N-C₆H₃(NHCOCH₃)-N(C₂H₅)₂ | 600 | reddish blue |
| 33 | 6-O₂N-benzo[b]thiophene-3-CN, 2-N=N-C₆H₃(CH₃)-N((CH₂)₃CH₃)₂ | 608 | reddish blue |
| 34 | 6-O₂N-benzo[b]thiophene-3-CN, 2-N=N-C₆H₃(NHCOCH₃)-X; X = 50% N(C₂H₅)₂, 50% N(C₃H₇)₂ | | reddish blue |
| 35 | 6-O₂N-benzo[b]thiophene-3-CN, 2-N=N-C₆H₃(NHCOCH₃)-N(C₂H₄OCH₃)₂ | | reddish blue |

| Example No. | | $\lambda_{max}$ (DMF) | Hue on polyester |
|---|---|---|---|
| 36 | | | strongly reddish blue |
| 37 | | | reddish blue |
| 38 | | | red violet |
| 39 | | | reddish violet |
| 40 | | | blue |
| 41 | | | blue |
| 42 | | | blue |
I claim:
1. A process for preparing a 2-aminothiophene of the formula
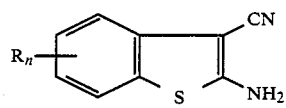
in which R denotes a substituent selected from the group consisting of F, Cl, Br, I, $C_1$–$C_4$-alkyl, $NO_2$, CN, $SO_2$-$C_1$–$C_4$-alkyl and $CF_3$ and n is a number from 0 to 4, comprising reacting a thioamide of the formula

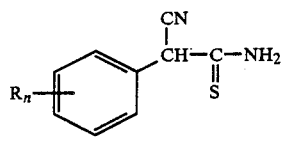

in which
R and n have the abovementioned meanings, with a dehydrogenating agent at a temperature of $-20°$ C. to 100° C. in the presence of an inert solvent to form a thiophene ring.

2. A process according to claim 1, wherein a halogen or halogen-eliminating compound is used as the dehydrogenating agent, said halogen-eliminating agent being N-bromosuccinimide.

3. A process according to claim 1, wherein bromine is used as the dehydrogenating agent.

4. A process according to claim 1, wherein the reaction is carried out in the presence of an acid acceptor.

5. A process according to claim 1, wherein the temperature is 10° C. to 30° C.

6. A process according to claim 1, wherein the solvent is methanol, ethanol, isopropanol, $CH_2Cl_2$, $C_2H_2Cl_2$, $CHCl_3$, $CCl_4$, toluene or chlorobenzene.

7. A process according to claim 1, wherein the acid acceptor is an organic base or an inorganic base.

8. A process according to claim 7, wherein the base is trialkylamine, pyridine, alkali metal oxides, alkaline earth metal oxides, hydroxides or carbonates.

* * * * *